US012765820B2

(12) United States Patent
Zakariaie et al.

(10) Patent No.: US 12,765,820 B2
(45) Date of Patent: Oct. 20, 2026

(54) OCULAR SYSTEM FOR DIAGNOSING AND MONITORING MENTAL HEALTH

(71) Applicant: Senseye, Inc., Austin, TX (US)

(72) Inventors: David Bobbak Zakariaie, Austin, TX (US); Lauren Caitlin Limonciello, Austin, TX (US); Veronica Choi, Austin, TX (US); Stephen Parvaresh, Austin, TX (US)

(73) Assignee: Senseye, Inc., Austin, TX (US)

( * ) Notice: Subject to any disclaimer, the term of this patent is extended or adjusted under 35 U.S.C. 154(b) by 1074 days.

(21) Appl. No.: 17/655,977

(22) Filed: Mar. 22, 2022

(65) Prior Publication Data

US 2022/0211310 A1 Jul. 7, 2022

Related U.S. Application Data

(63) Continuation-in-part of application No. 17/247,636, filed on Dec. 18, 2020, now Pat. No. 11,640,572, and (Continued)

(51) Int. Cl.

*A61B 5/16* (2006.01)
*A61B 3/14* (2006.01)

(Continued)

(52) U.S. Cl.

CPC .............. *A61B 5/163* (2017.08); *A61B 3/145* (2013.01); *A61B 5/0205* (2013.01); *A61B 5/165* (2013.01);

(Continued)

(58) Field of Classification Search

CPC ....... A61B 5/163; A61B 3/145; A61B 5/0205; A61B 5/165; A61B 5/7267; A61B 5/024;

(Continued)

(56) References Cited

U.S. PATENT DOCUMENTS

| | | | |
|---|---|---|---|
| 7,614,745 B2 | 11/2009 | Waldorf et al. |
| 8,531,354 B2 | 9/2013 | Woodard |

(Continued)

FOREIGN PATENT DOCUMENTS

| | | |
|---|---|---|
| JP | 2006-525829 A | 11/2006 |
| UA | 116785 U | 6/2017 |

(Continued)

OTHER PUBLICATIONS

Krafka, K. et al., "Eye Tracking for Everyone," 2016 IEEE Conference on Computer Vision and Pattern Recognition, Jun. 18, 2016, The Institute of Electrical and Electronics Engineers, Inc., Las Vegas, Nevada, p. 2176-2184.

(Continued)

*Primary Examiner* — Jennifer Robertson
*Assistant Examiner* — Elina Sohyun Jang
(74) *Attorney, Agent, or Firm* — Orbit IP, LLP; Marc G. Martino

(57) ABSTRACT

A method of measuring non-invasive ocular metrics is used to diagnose a mental health state of a patient. The method includes presenting a stimuli on an electronic display screen and recording a video of at least one eye of a patient by a video camera. The stimuli is configured to elicit a change in an ocular signal of the patient's eye. Software processes image frames of the video through a series of optimized algorithms configured to isolate and quantify the at least one ocular signal by applying an image mask isolating components. An algorithm estimates a probability of a mental health state based on the change in the at least one ocular signal. The estimated mental health state can be shown to the patient or to a mental health professional.

22 Claims, 2 Drawing Sheets

Related U.S. Application Data a continuation-in-part of application No. 17/247,634, filed on Dec. 18, 2020, now Pat. No. 11,928,632, and a continuation-in-part of application No. 17/247,637, filed on Dec. 18, 2020, now Pat. No. 12,265,935, and a continuation-in-part of application No. 17/247,635, filed on Dec. 18, 2020.

(60) Provisional application No. 63/200,696, filed on Mar. 23, 2021.

(51) Int. Cl.

| | |
|---|---|
| ***A61B 5/00*** | (2006.01) |
| ***A61B 5/0205*** | (2006.01) |
| ***A61B 5/024*** | (2006.01) |
| ***A61B 5/08*** | (2006.01) |
| ***G16H 20/70*** | (2018.01) |
| ***G16H 40/67*** | (2018.01) |
| ***G16H 50/20*** | (2018.01) |

(52) U.S. Cl.
CPC ........... *A61B 5/7267* (2013.01); *G16H 20/70* (2018.01); *G16H 40/67* (2018.01); *G16H 50/20* (2018.01); *A61B 5/024* (2013.01); *A61B 5/0816* (2013.01)

(58) Field of Classification Search
CPC ..... A61B 5/0816; A61B 3/0025; A61B 3/113; G16H 20/70; G16H 40/67; G16H 50/20; G16H 30/40
See application file for complete search history.

(56) References Cited

U.S. PATENT DOCUMENTS

| | | | | |
|---|---|---|---|---|
| 9,357,918 B1 | 6/2016 | Cohen | | |
| 9,357,966 B1 | 6/2016 | Cohen | | |
| 2004/0174496 A1 | 9/2004 | Ji et al. | | |
| 2009/0216092 A1 | 8/2009 | Waldorf et al. | | |
| 2010/0324454 A1 | 12/2010 | Kircher et al. | | |
| 2011/0066082 A1 | 3/2011 | Duffy | | |
| 2014/0148728 A1* | 5/2014 | Eizenman | A61B 5/165 | 600/558 |
| 2014/0178843 A1 | 6/2014 | Smyth | | |
| 2015/0070653 A1* | 3/2015 | Brown, Jr. | A61B 3/113 | 351/205 |
| 2017/0100032 A1 | 4/2017 | Zakariaie et al. | | |
| 2017/0119296 A1 | 5/2017 | Macknik et al. | | |
| 2017/0231490 A1* | 8/2017 | Toth | G16H 40/63 | 600/558 |
| 2018/0160959 A1 | 6/2018 | Wilde et al. | | |
| 2019/0239791 A1 | 8/2019 | Beck et al. | | |
| 2020/0060598 A1* | 2/2020 | Palti-Wasserman | A61B 5/163 | |
| 2020/0401938 A1 | 12/2020 | Etkin et al. | | |

FOREIGN PATENT DOCUMENTS

| | | |
|---|---|---|
| WO | 2007/131076 A2 | 11/2007 |
| WO | 2013/102768 A1 | 7/2013 |

OTHER PUBLICATIONS

Holzman, Philip S. et al., "Eye-Tracking Dysfunctions in Schizophrenic Patients and Their Relatives," Archives of General Psychiatry, Aug. 1, 1974, vol. 31, No. 2, p. 143-151.

Felmingham, Kim, "Eye Tracking and PTSD," chapter in Comprehensive Guide to Post-Traumatic Stress Disorders, Jun. 13, 2016, Springer International Publishing, Switzerland, p. 1241-1256.

Alexander et al. "California Verbal Learning Test: Performance by Patients with Focal Frontal and Non-frontal Lesions." Brain, vol. 126, No. 6, 2003, 1493-1503. https://doi.org/10.1093/brain/awg128.

Anderson, Kristen Joan, "Impulsitivity, Caffeine, and Task Difficulty: A within—Subjects Test of the Yerkes-Dodson Law", Personality and Individual Differences, vol. 16, No. 6, 1994, 813-29. https://doi.org/10.1016/0191-8869(94)90226-7.

Chaby et al. "Can We Understand How Developmental Stress Enhances Performance Under Future Threat with the Yerkes-Dodson law?", Communicative & Integrative Biology, vol. 8, No. 3, 2015, e1029689-e1029689, doi:10.1080/19420889.2015.1029689.

Cohen et al. "On the Functional Role of the Hippocampal System in Memory", Memory, Amnesia, and the Hippocampal System, 1993, pp. 285-290, The MIT Press, Cambridge, Massachusetts.

Dimitrov et al. "Associative Learning Impairments in Patients with Frontal Lobe Damage" Brain and Cognition, vol. 41, No. 2, 1999, 213-230. https://doi.org/10.1006/brcg.1999.1121.

Ebitz et al. "Selective Modulation of the Pupil Light Reflex by Microstimulation of Prefrontal Cortex", The Journal of Neuroscience, vol. 37, No. 19, May 10, 2017, 5008-5018. doi:10.1523/jneurosci.2433-16.2017.

Eslinger et al. "Altered Serial Position Learning After Frontal Lobe Lesion", Neuropsychologia, vol. 32, No. 6, 1994, 729-739. doi:10.1016/0028-3932(94)90032-9.

Hampson et al. "Neural Correlates of Fast Pupil Dilation in Non-human Primates: Relation to Behavioral Performance and Cognitive Workload", Behavioural Brain Research, vol. 212, No. 1, 2010, 1-11. doi:10.1016/j.bbr.2010.03.011.

Jetter et al. "A Verbal Long Term Memory Deficit in Frontal Lobe Damaged Patients", Cortex, vol. 22, No. 2, 1986, 229-242. doi:10.1016/s0010-9452(86)80047-8.

Jonides et al. "The Mind and Brain of Short-Term Memory", Annual Review of Psychology, vol. 59, No. 1, 2008, 193-224. doi:10.1146/annurev.psych.59.103006.093615.

Joshi et al. "Relationships between Pupil Diameter and Neuronal Activity in the Locus Coeruleus, Colliculi, and Cingulate Cortex", Neuron, vol. 89, 2016, 1-14. doi:10.1016/j.neuron.2015.11.028.

Kardon et al. "Segmental Denervation and Reinnervation of the Iris Sphincter as Shown by Infrared Videographic Transillumination", Ophthalmology, vol. 105, No. 2, 1997, 313-321, 10.1016/s0161-6420(98)93328-0.

Kesner et al. "Item and Order Dissociation in Humans with Prefrontal Cortex Damage", Neuropsychologia, vol. 32, No. 8, 1994, 881-891, doi:10.1016/0028-3932(94)90040-x.

Kucewicz et al. "Pupil Size Reflects Successful Encoding and Recall of Memory in Humans", Scientific Reports, vol. 8, No. 1, 2018, 7 pages, doi:10.1038/s41598-018-23197-6.

Marshall, Sandra P. "The Index of Cognitive Activity: Measuring Cognitive Workload." In Proceedings of the IEEE 7th Conference on Human Factors and Power Plants, 2002, 7-7, https://doi.org/10.1109/HFPP.2002.1042860.

McAndrews et al. "The Frontal Cortex and Memory for Temporal Order", Neuropsychologia, vol. 29, No. 9, 1991, 849-859, https://doi.org/10.1016/0028-3932(91)90051-9.

Moscovitch et al. "Frontal Lobes, Memory, and Aging", Annals of the New York Academy of Sciences, vol. 769, No. 1, 1995, 119-150, https://doi.org/10.1111/j.1749-6632.1995.tb38135.x.

Nakayama et al. "Frequency Analysis of Task Evoked Pupillary Response and Eye-Movement", In Proceedings of the 2004 Symposium on Eye Tracking Research & Applications, 2004, 71-76, https://doi.org/10.1145/968363.968381.

Peysakhovich et al. "Frequency Analysis of a Task-Evoked Pupillary Response: Luminance-independent Measure of Mental Effort", International Journal of Psychophysiology, vol. 97, No. 1, 2015, 30-37, doi:10.1016jijpsycho.2015.04.019.

Peysakhovich et al. "The Impact of Luminance on Tonic and Phasic Pupillary Responses to Sustained Cognitive Load", International Journal of Psychophysiology, vol. 112, 2017, 40-45. doi:10.1016/j.ijpsycho.2016.12.003.

Reiner et al. "Estimating Mental Workload through Event-related Fluctuations of Pupil Area During a Task in a Virtual World", International Journal of Psychophysiology, vol. 93, No. 1, 2014, 7 Pages, doi:10.1016/j.ijpsycho.2013.11.002.

(56) References Cited

OTHER PUBLICATIONS

Schlag et al. "Supplementary Eye Field: Influence of Eye Position on Neural Signals of Fixation", Experimental Brain Research, vol. 90, No. 2, 1992, 302-306, doi:10.1007/bf00227242.
Stuss et al. "Organizational Strategies with Unilateral or Bilateral Frontal Lobe Injury in Word Learning Tasks", Neuropsychology, vol. 8, No. 3, 1994, 355-373, doi:10.1037/0894-4105.8.3.355.
Swick et al. "Is Prefrontal Cortex Involved in Cued Recall? A Neuropsychological Test of PET Findings", Neuropsychologia, vol. 34, No. 10, 1996, 1019-1028, doi:10.1016/0028-3932(96)00011-5.
Yerkes et al. "The Relation of Strength of Stimulus to Rapidity of Habit-formation", Journal of Comparative Neurology and Psychology, vol. 18, No. 5, 1908, 459-482, doi:10.1002/cne.920180503.

* cited by examiner

FIG. 1
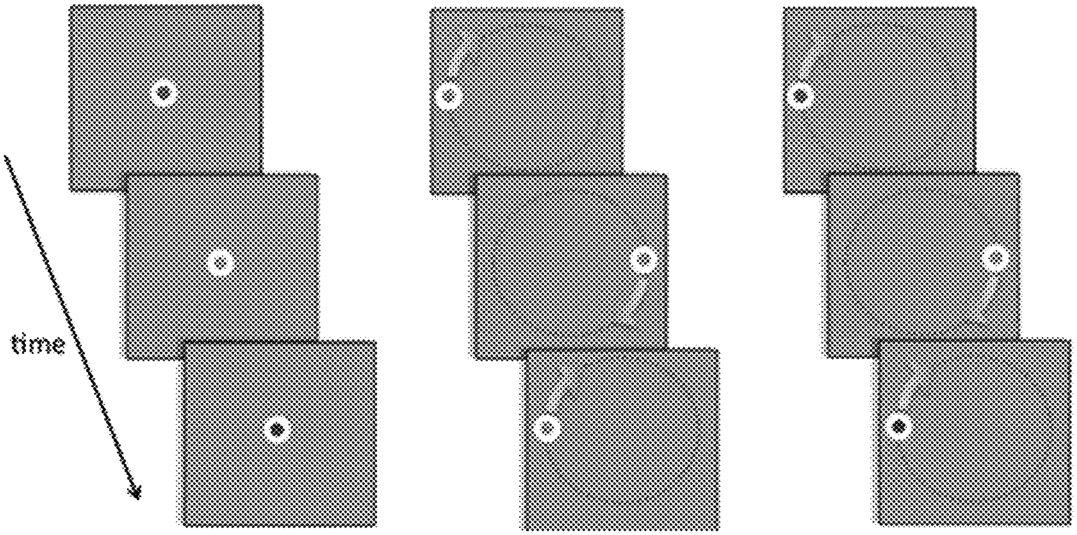
FIG. 2
| | Minimum | Maximum | Recommended |
|---|---|---|---|
| Screen Size (Diagonal) | 5.7 | 6.8 | 5.7 |
| Pixels Per Inch (PPI) | 412 | * | 443+ |
| Android OS (version) | 10 | * | 11+ |
| iOS (Version) | iOS 14 | * | iOS 15+ |
| Windows (Version) | 10 | * | 11 |
| Front-Facing Sensor[1] | 8MP / 1080p / 30fps | * / 1080p / 60fps | 8MP / 1080p / 30fps |
| Screen Refresh Rate (Hz) | 90 | 120 | 90 |
| RAM (GB) | 4 | * | 6+ |
| Available Storage (GB) | 1 | * | 2+ |
FIG. 3

OCULAR SYSTEM FOR DIAGNOSING AND MONITORING MENTAL HEALTH

CROSS-REFERENCE TO RELATED APPLICATIONS

This continuation-in-part application claims priority to provisional application 63/200,696 filed Mar. 23, 2021, the entire contents of which are hereby incorporated in full by this reference. This continuation-in-part application also claims priority to application Ser. No. 17/247,634 filed Dec. 18, 2020; application Ser. No. 17/247,635 filed Dec. 18, 2020; application Ser. No. 17/247,636 filed Dec. 18, 2020; and application Ser. No. 17/247,637 filed Dec. 18, 2020, the entire contents of which are hereby incorporated in full by this reference.

FIELD OF THE INVENTION

The present invention generally relates to an ocular system for monitoring mental health. More particularly, the present invention relates to an ocular system that can visually scan a user's (patient's) eye movements (i.e., gaze) combined with ocular activity in the eye (i.e., pupil dilation, iris dilator and sphincter muscle dilation and constriction) to diagnose a mental health condition that can be displayed to the user or a mental health professional.

BACKGROUND OF THE INVENTION

The prevalence of posttraumatic stress disorder (PTSD) has been estimated to be as high as 23% in veterans returning from Iraq and Afghanistan. The lifetime incidence of PTSD for all US adults is estimated at 6.8%. However, PTSD diagnosis requires a structured clinical interview with a mental health clinician and incorporating screening tools such as the Clinician-Administered PTSD Scale for DSM-5 (CAPS-5), which is time-consuming and labor-intensive, and heavily relies on subjective self-reporting from the patient. Given the prevalence of PTSD and the need for a quick, effective, objective and accurate diagnostic tool (particularly in the high-risk population such as military personnel) Senseye has developed a Machine Learning powered software as a medical device (SAMD) to quantitatively assess the presence and severity of PTSD symptoms measured through computer vision and analytic techniques.

PTSD is associated with adverse aggressive behaviors, emotional constrictions, and social withdrawal, with evidence of impaired fear extinction and neuroplasticity, and is linked with impaired eye reactivity, autonomous nervous system (ANS) reactivity, and increased activity, neurovascular inflammation, sleep disturbances, suicidality, and major cardiovascular events. (9-18) In fact, prior research has demonstrated that PTSD patients could be accurately discriminated from control participants based on their pupil reactivity to visual and auditory threat stimuli. (19) This atypical reactivity may also be manifested in a simple reflexive response, as sympathetic overdrive would result in reduced constriction velocity and amplitude to light because the dilator is overactive. (19-22)

Prior studies have shown that impaired oculomotor reactions measured by eye-tracking and impaired ANS reactivity measured by pupil light reflex in response to threat-relevant stimuli can directly assess PTSD's severity of symptoms. (19-22)

Clinician-Administered PTSD Scale for DSM-5 (CAPS-5), UCLA PTSD reaction index (RI), as gold standards tools in the diagnosis of PTSD, have been extensively validated against standardized structural clinical interview across sex, age groups, and cultures with high feasibility, acceptability to assess core PTSD symptoms, and facilitating risk stratification and outcome prediction in individuals at risk for PTSD. (23, 24)

Deep machine learning and artificial intelligence (AI) can detect eye reactivity, sensory perception, and engagement. (9-15) AI evaluates an individual's response to digitally created scenarios threat and neutral stimuli into the real-world environment; it provides the unique opportunity for real-time detection of PTSD. (9-15) The lack of a scalable real-time operator-independent tool to assess the presence and severity of PTSD and monitoring response to intervention significantly limit the early identification and management of individuals at risk for PTSD. (17, 25-28) Senseye's Operator-independent Ocular Brain-Computer Interface (OBCI) can eliminate these limitations and add a safe, viable adjunct to standardized structured clinical interviews to assess the real-time presence and severity of PTSD and monitor response to interventions. (29) With the emergence of deep machine learning technology that is now possible to detect and monitor PTSD in real-time with Senseye's CV and Machine Learning Algorithms, we propose to utilize a machine learning-powered software as a diagnostic device to quantitatively assess the presence and severity of PTSD symptoms measured through computer vision and proprietary analytic techniques developed by Senseye.

SUMMARY OF THE INVENTION

A method of measuring non-invasive ocular metrics to diagnose a mental health state of a patient comprises the steps of: providing a video camera, an electronic display screen, a hardware system and a software configured to run on the hardware system, wherein the video camera and the electronic display screen are connected to the hardware system and controlled by the software; providing access to the patient to the electronic display screen to interact with the software, wherein the video camera is located near or as part of the electronic display screen configured to non-invasively record at least one eye of the patient when viewing the electronic display screen; presenting a stimuli on the electronic display screen by the software; during presenting the stimuli, recording a video of the at least one eye of the patient by the video camera; wherein the stimuli comprises an oculomotor task or oculomotor stimuli configured to elicit a change in at least one ocular signal of the at least one eye of the patient, the stimuli comprising a stimuli image, a series of stimuli images or a stimuli video for passive watching by the patient configured to elicit the change in the at least one ocular signal; wherein the at least one ocular signal is selected from the following group of a(n): eye movement, gaze location X, gaze location Y; saccade rate, saccade peak velocity, saccade average velocity, saccade amplitude, fixation duration, fixation entropy (spatial), gaze deviation (polar angle), gaze deviation (eccentricity), re-fixation, smooth pursuit, smooth pursuit duration, smooth pursuit average velocity, smooth pursuit amplitude, scan path (gaze trajectory over time), pupil diameter, pupil area, pupil symmetry, velocity (change in pupil diameter), acceleration (change in velocity), jerk (pupil change acceleration), pupillary fluctuation trace, pupil area constriction latency, pupil area constriction velocity, pupil area dilation duration, spectral features, iris muscle features, iris muscle group identification, iris muscle fiber contractions, iris sphincter identification, iris dilator identification, iris sphincter symmetry, pupil and iris centration vectors, blink rate, blink duration, blink latency, blink velocity, partial blink rate, partial blink duration, blink entropy (deviation from periodicity), sclera segmentation, iris segmentation, pupil segmentation, stroma change detection, percent eyes closed, eyeball area (squinting), iridea changes; wherein the hardware system comprises a processor configured to run a machine learning classification model and a computer vision model; processing, by the computer vision model, image frames of the video of the at least one ocular signal through a series of optimized algorithms configured to isolate and quantify the at least one ocular signal by applying an image mask isolating components of the at least one eye of the patient; estimating, by an algorithm run by the machine learning classification model, a probability from the at least one ocular signal that it represents the mental health state; and displaying, after the processing, the mental health state estimated by the software of the patient to the patient, or, sending the mental health state to a mental health professional via an electronic communication.

The mental health state may comprise a mental health disorder, a substance abuse disorder, a post-traumatic stress disorder, an anxiety disorder, a depressive disorder, an acute stress disorder or an acute stress reaction.

The at least one ocular signal may comprise at least two ocular signals or at least three ocular signals.

The method may be repeated after an initial diagnosis to measure a severity of the mental health disorder over a period of time.

The method may be repeated after an initial diagnosis to measure a severity of the mental health disorder over a period of time while the patient is receiving treatment in order to measure a treatment efficacy.

The method may include storing the mental health state of the patient in a retrievable data retention system.

The video camera, the electronic display screen, the hardware system and the software may be configured to run on the hardware system which are all part of an electronic mobile device, a tablet, a desktop computer or a laptop computer.

The video camera and electronic display screen may be remotely disposed in relation to the hardware system and software configured to run the hardware system. For example, the hardware system and software may comprise a cloud-based system.

The video camera may be a webcam, a cell phone camera, or any other video camera with sufficient resolution and frame rate. The sufficient frame rate may be 30 frames per seconds and the sufficient resolution may be 100 pixels per inch.

The method may include the step of measuring heart rate, wherein the estimating, by the algorithm run by the machine learning classification model, of the probability includes information from both the at least one ocular signal and the heart rate.

The method may include the step of measuring respiration, wherein the estimating, by the algorithm run by the machine learning classification model, of the probability includes information from both the at least one ocular signal and the respiration.

Other features and advantages of the present invention will become apparent from the following more detailed description, when taken in conjunction with the accompanying drawings, which illustrate, by way of example, the principles of the invention.

BRIEF DESCRIPTION OF THE DRAWINGS

The accompanying drawings illustrate the invention. In such drawings:

FIG. 1 illustrates an ocular stimuli using screen color and luminance during the four phases of the pupillary light response stimuli;

FIG. 2 illustrates an ocular stimuli using a smooth pursuit task stimuli where a stimulus moves in a circular pattern;

FIG. 3 is a table displaying the minimum requirements for the present invention to function correctly;

DETAILED DESCRIPTION OF THE PREFERRED EMBODIMENTS

Ocular System for Monitoring Mental Health

Figure 4A:
FIG. 4A illustrates an example of an ocular stimuli in the form of a still image designed to create a change in at least one ocular signal of the patient.

Overview: Senseye Mental Health Monitoring (SMHM) operates at the intersection of mental health therapies and technology. It provides a new, objective, method of quantifying mental health states and the impacts of therapeutic techniques. The system uses non-invasive ocular measures, to measure the Sympathetic and Parasympathetic Nervous systems to identify and track occurrences of mental health disorders manifesting themselves in disruptions of the sympathetic nervous system (such as Anxiety, Depression and PTSD). SMHM algorithms monitor and classify these mental states on an individual basis. SMHM algorithms are not only able to identify mental health disorders, but are also able to track mental health status over time. SHMH can aid in adapting therapeutic interventions, from talk therapy to microdosing, to an individual's unique mental state. This level of adaptive therapy and monitoring provides accelerated treatment while ensuring the compliance and utility of the intervention.

Product Function: The Senseye system is designed to run on a variety of hardware options. The eye video can be acquired by a webcam, cell phone camera, or any other video camera with sufficient resolution and frame rate. For example, a sufficient frame rate is 30 or 60 fps but could be lower over time with the improvement in technology. Also, the sufficient resolution is 240 by 240-pixel box over the eyes, but could be as low as a 100 pixels per inch. The stimuli can be presented on a cell phone, tablet, or laptop screen or a standard computer monitor. The necessary hardware to run the software is neural-network-capable fpgas (Field Programmable Gate Array), asics (application-specific integrated circuit) or accelerated hardware, either within the device or on a server accessed through an API.

The Senseye assessment begins with the user initiating the process by logging in to the system. This can be achieved by typing a username and password issued to them by their HCP (HealthCare Provider). In one embodiment, the user is presented with a series of oculomotor tasks and or stimuli. In another embodiment, the scan is designed to be more passive, so the user's eyes are recorded while they passively view a screen.

Signals: Senseye Mental Health Monitoring detection relies on ocular signals to make its classifications. These include:

Eye Movement
Gaze location X
Gaze location Y
Saccade Rate
Saccade Peak Velocity
Saccade Average Velocity
Saccade Amplitude
Fixation Duration
Fixation Entropy (spatial)
Gaze Deviation (Polar Angle)
Gaze Deviation (Eccentricity)
Re-Fixation
Smooth Pursuit
Smooth Pursuit Duration
Smooth Pursuit Average Velocity
Smooth Pursuit Amplitude
Scan Path (gaze trajectory over time)
Pupil Diameter
Pupil Area
Pupil Symmetry
Velocity (change in Pupil diameter)
Acceleration (change in velocity)
Jerk (pupil change acceleration)
Pupillary Fluctuation Trace
Pupil Area Constriction Latency
Pupil Area Constriction Velocity
Pupil Area Dilation Duration
Spectral Features
Iris Muscle Features
Iris Muscle Group Identification
Iris Muscle Fiber Contractions
Iris Sphincter Identification
Iris Dilator Identification
Iris Sphincter Symmetry
Pupil and Iris Centration Vectors
Blink Rate
Blink Duration
Blink Latency
Blink Velocity
Partial Blink Rate
Partial Blink Duration
Blink Entropy (deviation from periodicity)
Sclera Segmentation
Iris Segmentation
Pupil Segmentation
Stroma Change Detection
Percent Eyes Closed
Eyeball Area (squinting)
Iridea Changes
Heart Rate Variability
Respiration Rate
Facial expressions The signals are acquired using a multistep process designed to extract nuanced information from the eye. Image frames from video data are processed through a series of optimized algorithms designed to isolate and quantify structures of interest. These isolated data are further processed using a mixture of automatically optimized, hand parameterized, and non-parametric transformations and algorithms.

Disorder Detection: The SMHM software is capable of working on any device with a front facing camera (tablet, phone, computer, etc.). The SMHM software draws on previous scientific findings (D'Hondt et al., 2014; Ferneyhough et al., 2013; Kattoulas et al., 2011; Laretzaki et al., 2011; Nagai et al., 2002; Quigley et al., 2012; Strollstorf et al., 2013; Young et al., 2012) and uses anatomical and physiological signals extracted from images to predict different mental states through optimized algorithms. The algorithms provide an estimated probability that the input data represents a particular disordered mental state and may identify the presence of one or more states. Image signals are run through a series of data processing operations to extract signals and estimations. Multiple image masks are first applied, isolating components of the eyes as well as facial features allowing various metrics to be extracted from the image in real-time. From the image filters, pertinent signals are extracted through transformation algorithms supporting the final estimation of mental states. Multiple data streams and estimations can be made in a single calculation, and mental state signals may stem from combinations of multiple unique processing and estimation algorithms. The mental state output is directly linked to the stimulus (video and/or images and/or blank screen shown) by relating processing signals during the stimulus. The software can display, immediately after the screening, the mental state of the individual.

The SHMH software can operate on a longitudinal basis as well. As users continue to check in with the software, their states over time are monitored for information as to how frequently a user experiences disordered mental states. The system stores this information unique to each user. This provides additional information to users and treatment specialists.

Therapeutic effectiveness and intervention: The capability to track a user longitudinally and remotely allows for analysis of the effectiveness of therapeutic interventions. As a user undergoes therapy the system continues to output information about mental states stored longitudinally for each user. This allows the user and other stakeholders to objectively monitor improvements in condition via changes in ocular signals. Therapeutic interventions are not limited and may include traditional therapeutic methods as well as analysis of patient response to smart dosing. Ocular metrics can be taken at different levels of dosing and help treatment specialists converge quicky on effective treatment levels.

Detecting, Diagnosing and Monitoring Substance Use Disorders in an Objective and Noninvasive Manner Overview: Senseye Substance Use Disorder Diagnosis (SSUDD) uses non-invasive ocular measures of brain state and physiology to identify and track substance use disorders. It is able to differentiate between different substances, specifically between substances of abuse and those used for therapeutic intervention, and thus serve as a therapeutic monitoring tool. By monitoring ocular metrics throughout different levels of drug based therapeutic intervention, SSUDD aids in adapting the interventions to an individual's unique case. This level of monitoring provides accelerated treatment while ensuring the compliance and utility of the intervention.

Product Function: The Senseye system is designed to run on a variety of hardware options. The eye video can be acquired by a webcam, cell phone camera, or any other video camera with sufficient resolution and frame rate. The stimuli can be presented on a cell phone, tablet, or laptop screen or a standard computer monitor. The necessary hardware to run the software is neural-network-capable fpgas, asics or accelerated hardware; either within the device or on a server accessed through an API.

The Senseye assessment begins with the user initiating the process by logging in to the system. This can be achieved by typing a username and password, or using facial recognition. In one embodiment, the user is presented with a series of oculomotor tasks and or stimuli. In another embodiment, the scan is designed to be more passive, so the user's eyes are recorded while they passively view a screen.

Signals: Senseye Substance Use Disorder Detection relies on ocular signals to make its classifications. These include:

Eye Movement
Gaze location X
Gaze location Y
Saccade Rate
Saccade Peak Velocity
Saccade Average Velocity
Saccade Amplitude
Fixation Duration
Fixation Entropy (spatial)
Gaze Deviation (Polar Angle)
Gaze Deviation (Eccentricity)
Re-Fixation
Smooth Pursuit
Smooth Pursuit Duration
Smooth Pursuit Average Velocity
Smooth Pursuit Amplitude
Scan Path (gaze trajectory over time)
Pupil Diameter
Pupil Area
Pupil Symmetry
Velocity (change in Pupil diameter)
Acceleration (change in velocity)
Jerk (pupil change acceleration)
Pupillary Fluctuation Trace
Pupil Area Constriction Latency
Pupil Area Constriction Velocity
Pupil Area Dilation Duration
Spectral Features
Iris Muscle Features
Iris Muscle Group Identification
Iris Muscle Fiber Contractions
Iris Sphincter Identification
Iris Dilator Identification
Iris Sphincter Symmetry
Pupil and Iris Centration Vectors
Blink Rate
Blink Duration
Blink Latency
Blink Velocity
Partial Blink Rate
Partial Blink Duration
Blink Entropy (deviation from periodicity)
Sclera Segmentation
Iris Segmentation
Pupil Segmentation
Stroma Change Detection
Percent Eyes Closed
Eyeball Area (squinting)
Iridea Changes The signals are acquired using a multistep process designed to extract nuanced information from the eye. Image frames from video data are processed through a series of optimized computer vision algorithms designed to isolate and quantify structures of interest. These isolated data are further processed using a mixture of automatically optimized, hand parameterized, and non-parametric transformations and algorithms.

Substance use detection: The SSUDD software is capable of working on any device with a front facing camera (tablet, phone, computer, etc.). The SSUDD software uses anatomical signals extracted from images to predict the levels of different substances present in a user through optimized algorithms. The algorithms provide an estimated probability that the input data represents presences of a particular substance and may identify the presence of one or more substances. Image signals are run through a series of data processing operations to extract signals and estimations. Multiple image masks are first applied, isolating components of the eyes as well as facial features allowing various metrics to be extracted from the image in real-time. From the image filters, pertinent signals are extracted through transformation algorithms supporting the final estimation of substance levels. Multiple data streams and estimations can be made in a single calculation, and substance presence signals may stem from combinations of multiple unique processing and estimation algorithms. Previous scientific research has shown links between ocular physiology and substances present in a person's system (Dhingra, Kaur, & Ram 2019; Fazari, 2011; Kaut, Oliver, Kornblum, & Cornelia, 2010; Merlin, 2008; Murillo, Crucilla, Schmittner, Hotchkiss, & Pickworth, 2004; Rottach, Wohlgemuth, Dzaja, Eggert, & Straube, 2002). In SSUDD, the substance level output is directly linked to the stimulus (video and/or images and/or blank screen shown) through analysis of ocular signals. The software can display, immediately after the screening, the presence or absence of opioids, alcohol or other substances of abuse.

Therapeutic effectiveness and intervention: Because the SSUDD is able to differentiate between substances, specifically substances of abuse and therapeutic substances, this allows for the application to be used to track compliance with therapeutic interventions. Not only are the readings informative, but the rate at which the user deviates from a set check-in schedule can provide information about their compliance with a therapeutic program. As a user undergoes therapy the system continues to output information about substance use, including use of therapeutic substances, and this is stored longitudinally for each user. This allows the user and other stakeholders, such as doctors and other therapists, to objectively monitor improvements in condition via changes in ocular signals.

An Objective Diagnostic and for Post-Traumatic Stress Disorder

Overview: The Senseye PTSD Diagnostic provides a new, objective, method of quantifying mental health states and the impacts of therapeutic techniques. It is the first of its kind tool allowing for the objective diagnosis of and continuous monitoring of PTSD. The tool can both diagnose PTSD as well as continuously monitor the patient via recurring scans it in order to monitor treatment response, changing severity and too predict treatment responses.

The system records video of the user's eyes while they perform various oculomotor tasks and/or passively view a screen. The ORM system also includes the software that presents the stimuli to the user. The system uses computer vision to segment the eyes and quantify a variety of ocular features. The ocular metrics then become inputs to a machine learning algorithm designed to diagnose the condition and report on its severity. The product's algorithms are not only able to identify anxiety-related mental health disorders, but are also able to track mental health status over time. SHMH can aid in adapting therapeutic interventions, from talk therapy to microdosing, to an individual's unique mental state. This level of adaptive therapy and monitoring provides accelerated treatment while ensuring the compliance and utility of the intervention.

Inputs and outputs: The primary input the Senseye system is video footage of the eyes of the user while they perform the oculomotor tasks presented by the system. The location and identity of visible anatomical features from the open eye (i.e., sclera, iris, and pupil) are classified in digital images in a pixel-wise manner via convolutional neural networks originally developed for medical image segmentation. Based on the output of the convolutional neural network, numerous ocular features are produced. These ocular metrics are combined with event data from the oculomotor tasks which provide context and labels. The ocular metrics and event data are provided to the machine learning algorithms which then return a result of a diagnosis or lack of, or "more information needed." This is achieved by quantifying the pupil and iris dynamics throughout the oculomotor tasks.

Signals: Senseye Mental Health Monitoring detection relies on ocular signals to make its classifications. These include:

Eye Movement
Gaze location X
Gaze location Y
Saccade Rate
Saccade Peak Velocity
Saccade Average Velocity
Saccade Amplitude
Fixation Duration
Fixation Entropy (spatial)
Gaze Deviation (Polar Angle)
Gaze Deviation (Eccentricity)
Re-Fixation
Smooth Pursuit
Smooth Pursuit Duration
Smooth Pursuit Average Velocity
Smooth Pursuit Amplitude
Scan Path (gaze trajectory over time)
Pupil Diameter
Pupil Area
Pupil Symmetry
Velocity (change in Pupil diameter)
Acceleration (change in velocity)
Jerk (pupil change acceleration)
Pupillary Fluctuation Trace
Pupil Area Constriction Latency
Pupil Area Constriction Velocity
Pupil Area Dilation Duration
Spectral Features
Iris Muscle Features
Iris Muscle Group Identification
Iris Muscle Fiber Contractions
Iris Sphincter Identification
Iris Dilator Identification
Iris Sphincter Symmetry
Pupil and Iris Centration Vectors
Blink Rate
Blink Duration
Blink Latency
Blink Velocity
Partial Blink Rate
Partial Blink Duration
Blink Entropy (deviation from periodicity)
Sclera Segmentation
Iris Segmentation
Pupil Segmentation
Stroma Change Detection
Percent Eyes Closed
Eyeball Area (squinting)
Iridea Changes
HRV from the Face The signals are acquired using a multistep process designed to extract nuanced information from the eye. Image frames from video data are processed through a series of optimized algorithms designed to isolate and quantify structures of interest. These isolated data are further processed using a mixture of automatically optimized, hand parameterized, and non-parametric transformations and algorithms.

Product Function: The Senseye PTSD system is designed to run on a variety of hardware options. The software is capable of working on any device with a front facing camera (tablet, phone, computer, etc.). The SMHM software draws on previous scientific findings (D'Hondt et al., 2014; Fernyhough et al., 2013; Kattoulas et al., 2011; Laretzaki et al., 2011; Nagai et al., 2002; Quigley et al., 2012; Strollstorf et al., 2013; Young et al., 2012) and uses anatomical and physiological signals extracted from images to predict different mental states through optimized algorithms. The algorithms provide an estimated probability that the input data represents a particular disordered mental state and may identify the presence of one or more states. Image signals are run through a series of data processing operations to extract signals and estimations. Multiple image masks are first applied, isolating components of the eyes as well as facial features allowing various metrics to be extracted from the image in real-time. From the image filters, pertinent signals are extracted through transformation algorithms supporting the final estimation of mental states. Multiple data streams and estimations can be made in a single calculation, and mental state signals may stem from combinations of multiple unique processing and estimation algorithms. The mental state output is directly linked to the stimulus (video and/or images and/or blank screen shown) by relating processing signals during the stimulus. The software can display, immediately after the screening, the mental state of the individual.

The software can operate on a longitudinal basis as well. As users continue to check in with the software, their states over time are monitored for information as to how frequently a user experiences disordered mental states. The system stores this information unique to each user. This provides additional information to users and treatment specialists.

Therapeutic effectiveness and intervention: The capability to track a user longitudinally and remotely allows for analysis of the effectiveness of therapeutic interventions. As a user undergoes therapy the system continues to output information about mental states stored longitudinally for each user. This allows the user and other stakeholders to objectively monitor improvements in condition via changes in ocular signals. Therapeutic interventions are not limited and may include traditional therapeutic methods as well as analysis of patient response to smart dosing. Ocular metrics can be taken at different levels of dosing and help treatment specialists converge quicky on effective treatment levels.

Description: The Senseye Device is an AI/MI based Software as a Medical Device. A patient views a series of stimuli in the form of ocular tasks on a mobile phone while we track their ocular movements in response to such stimuli. The methods described here are intended to provide the high-level composition of ocular screening tasks that form the basis of each experimental session. Final task composition and duration will likely be modified.

Ocular tasks known to elicit pupillary and eye movement dynamics of interest will be used. See FIG. 1 for some example tasks. In FIG. 1A, a pupillary light-response task is shown. In this task, participants stare at the center of a screen which changes in luminance and pupil response is measured. FIG. 1B shows smooth pursuit which measures the ability of participants to follow a moving stimulus with their eyes using accurate eye movements.

Other tasks include a task requiring participants to make saccadic eye movements toward randomly appearing targets on the screen, a task requiring free viewing of neutral and aversive images, and tasks measuring alertness or reaction time. All of these tasks are short in duration (less than 1 minute), but may be repeated multiple times within an experimental session, thereby requiring an onsite time commitment from participants of 5-30 minutes. The tasks can easily be deployed on mobile devices that the participants can take home for regular check-ins (5-10 minutes) throughout the day at specified intervals if required. Senseye intends to initially deploy the product with 10-15 ocular tasks in clinical trials to identify which 3-5 are the most accurate in PTSD diagnostics.

FIG. 1 illustrates screen color and luminance during the four phases of the pupillary light response stimuli. Each screen state lasts for 5 seconds.

FIG. 2 illustrates a smooth pursuit task stimuli. Stimulus moves in a circular pattern at a frequency of 0.166 Hz.

FIG. 3 is a table displaying the current minimum requirements for the present invention to function correctly. This is the minimum screen size, operating system and camera resolution required for the device to function currently. This will be improved over time.

Figure 4B:
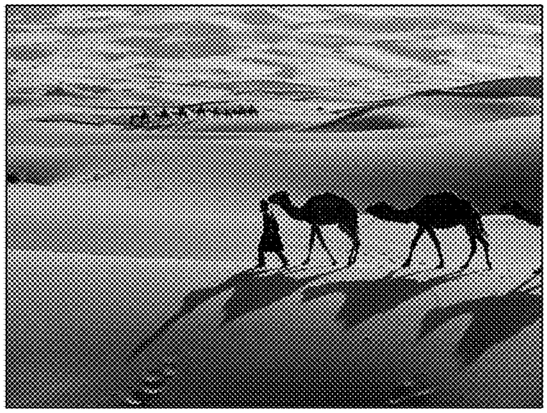
FIG. 4B illustrates another example of an ocular stimuli in the form of a still image designed to create a change in at least one ocular signal of the patient.
Figure 4C:
FIG. 4C illustrates another example of an ocular stimuli in the form of a still image designed to create a change in at least one ocular signal of the patient.
Figure 4D:
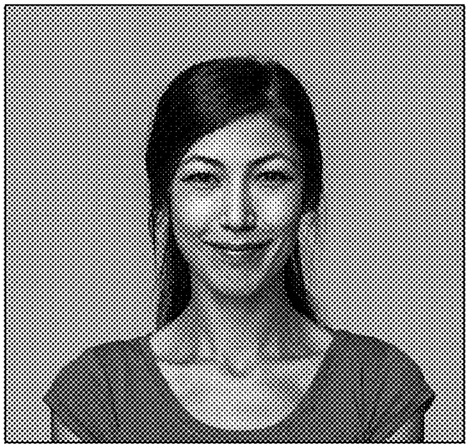
FIG. 4D illustrates another example of an ocular stimuli in the form of a still image designed to create a change in at least one ocular signal of the patient.
Figure 4E:
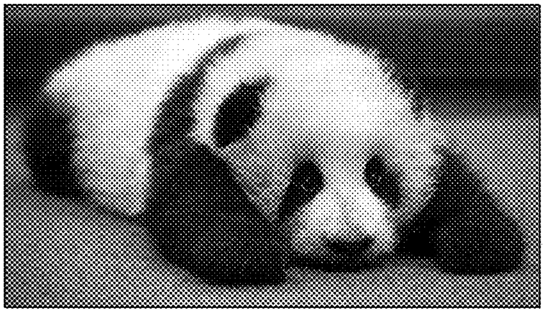
FIG. 4E illustrates another example of an ocular stimuli in the form of a still image designed to create a change in at least one ocular signal of the patient.

FIGS. 4A-4E illustrate examples of an ocular stimuli in the form of a still image designed to create a change in at least one ocular signal of the patient, which includes categories such as: positive, negative, negative with arousal, neutral, and facial expressions. These are example images of our affective image task where we show a selection of images from the above categories out of our database of several thousand images. the affective image task, which involves passive viewing of images that are both threatening and neutral in content. The user/patient will view a gray computer screen for 30 seconds followed by an image in 5-second intervals. The images will be an even split of neutral and threatening scenes presented in pseudo-random order.

Hardware: Onsite high-resolution data is collected using mobile phones with either their built-in cameras or an external camera plugged into the phone, or with cameras plugged into laptop computers. To utilize the features we have developed and optimize the performance of the device, we have picked a minimum list of requirements for use with the Senseye application as shown in FIG. 2. The Senseye application uses the front-facing (selfie) camera to record video.

It has been shown that pupil diameter changes in response to images differently if a patient has PTSD. However, to the inventor's knowledge, and based on the FDA's De Novo Classification for the device nobody has ever been able to build a product that works based on changes in pupil diameter. The present invention works because it is measuring all those things beyond just pupil size. Therefore, a system must be able to measure at least 2, 3, 4, 5, 10, 15, 20 or any "n" number ocular metrics beyond pupil size. While it is positive to use just one ocular metric to determine a mental health state, this may lead to a false positive such that the rate for a false determination would be too high. Thus, the inventors prefer to use a combination of ocular metrics to provide a more reliable determination of mental health state.

The inventors have developed computer vision algorithms capable of using normal cameras for the present invention. Accordingly, the entire contents of the following list of patent applications by the inventors are fully incorporated herein with this reference: application Ser. No. 17/247,634 filed Dec. 18, 2020; application Ser. No. 17/247,635 filed Dec. 18, 2020; application Ser. No. 17/247,636 filed Dec. 18, 2020; application Ser. No. 17/247,637 filed Dec. 18, 2020, and PCT application PCT/US20/70939 filed on Dec. 19, 2020. More specifically, these prior applications taught a method for generating NIR images from RGB cameras using generative adversarial networks and a combination of visible and IR light. Thus, the relevant text from those applications is repeated herein for convenience.

Continuing the theme of creating a mapping between subsurface iris structures visible in IR light onto surface structures seen in visible light, Senseye has developed a method of projecting iris masks formed on IR images onto the data extracted from visible light. This technique uses a generative adversarial network (GAN) to predict the IR image of an input image captured under visible light (see FIG. 14 of the prior applications). The CV mask is then run on the predicted IR image and overlaid back to the visible light image (see FIG. 15 of the prior applications).

Part of this method is generating a training set of images on which the GAN learns to predict IR images from visible light images (see FIG. 14 of the prior applications). Senseye has developed a hardware system and experimental protocol for generating these images. The apparatus consists of two cameras, one color sensitive, and one NIR sensitive (see numerals 16.1 and 16.2 in FIG. 16 of the prior applications). The two are placed tangent to one another such that a hot mirror forms a 45 degree angle with both (see numeral 16.3 in FIG. 16 of the prior applications). The centroid of the first surface of the mirror is equidistant from both sensors. Visible light passes straight through the hot mirror onto the visible sensor and NIR bounces off into the NIR sensor. As such, the system creates a highly optically aligned NIR and color image which can be superimposed pixel-for-pixel. Hardware triggers are used to ensure that the cameras are exposed simultaneously with error <1 uS.

FIG. 16 of the prior applications is a diagram of hardware design that captures NIR and visible light video simultaneously. Two cameras, one with a near IR sensor and one with a visible light sensor are mounted on a 45-degree angle chassis with a hot mirror (invisible to one camera sensor, and an opaque mirror to the other) to create image overlays with pixel-level accuracy.

Creating optically and temporally aligned visible and NIR datasets with low error allows Senseye to create enormous and varied datasets that do not need to be labelled. Instead of manual labelling, the alignment allows Senseye to use the NIR images as reference to train the color images against. Pre-existing networks already have the ability to classify and segment the eye into sclera, iris, pupil, and more, giving us the ability to use their outputs as training labels. Additionally, unsupervised techniques like pix-to-pix GANs utilize this framework to model similarities and differences between the image types. These data are used to create surface-to-surface, and/or surface-to-subsurface mapping of visible and invisible iris features.

Other methods being considered to properly filter the RGB spectrum so it resembles the NIR images, is the use of a simulation of the eye so that rendered images resembles both natural light and that in NIR light spectrum. The neural network structures would be similar to those listed previously (pix-to-pix) and the objective would be to allow for the sub cornea structures (iris and pupil) to be recovered and segmented properly despite the reflections or other artifacts caused by the interaction of the natural light spectrum (360 to 730 nm) with the particular eye.

The utility of the GAN is to learn a function that is able to generate NIR images from RGB images. The issues with RGB images derive from the degradation of contrast between pupil and iris specifically for darker eyes. What this means is that if there isn't enough light flooding the eye, the border of a brown iris and the pupil hole are indistinguishable due to their proximity in the color spectrum. In RGB space, because we do not control for a particular spectrum of light, we are at the mercy of another property of the eye which is that it acts as a mirror. This property allows for any object to appear as a transparent film on top of the pupil/iris. An example of this is you can make out a smaller version of a bright monitor on your eye given an rgb image. So the GAN acts as a filter. It filters out the reflections, sharpens boundaries, and due to its learned embedding, it is capable of restoring the true boundary of iris and pupil.

In furtherance of improving the present invention, the inventors have been able to make the present invention work with just a normal camera without use of the GAN. However, sometimes use of the GAN is still needed, but not always. Again, this is an area of constant improvement by the inventors of the instant application.

Although several embodiments have been described in detail for purposes of illustration, various modifications may be made to each without departing from the scope and spirit of the invention. Accordingly, the invention is not to be limited, except as by the appended claims.

What is claimed is:

1. A method of measuring non-invasive ocular metrics to diagnose a mental health state of a patient, the method comprising the steps of:

providing a video camera, an electronic display screen, a hardware system and a software configured to run on the hardware system, wherein the video camera and the electronic display screen are connected to the hardware system and controlled by the software;

providing access to the patient to the electronic display screen to interact with the software, wherein the video camera is located near or as part of the electronic display screen configured to non-invasively record at least one eye of the patient when viewing the electronic display screen;

presenting a first stimuli and a second stimuli on the electronic display screen by the software;

during presenting the first and the second stimuli, recording a video of the at least one eye of the patient by the video camera;

wherein the first stimuli comprises an oculomotor task or oculomotor stimuli configured to elicit a change in at least one ocular signal of the at least one eye of the patient, the first stimuli comprising a pupillary light response stimuli and/or a smooth pursuit task stimuli for passive watching by the patient configured to elicit the change in the at least one ocular signal;

wherein the second stimuli is configured to elicit a change in the at least one ocular signal of the at least one eye of the patient, the second stimuli comprising an affective image task involving passive viewing of a series of still images for passive watching by the patient that are configured to be threatening or neutral in content to the patient, wherein the affective image task comprises images pre-classified as threatening or neutral according to a predefined affective image database or labeling protocol stored in the system;

wherein the at least one ocular signal is selected from the following group of a(n):

eye movement, gaze location X, gaze location Y; saccade rate, saccade peak velocity, saccade average velocity, saccade amplitude, fixation duration, fixation entropy (spatial), gaze deviation (polar angle), gaze deviation (eccentricity), re-fixation, smooth pursuit, smooth pursuit duration, smooth pursuit average velocity, smooth pursuit amplitude, scan path (gaze trajectory over time), pupil diameter, pupil area, pupil symmetry, velocity (change in pupil diameter), acceleration (change in velocity), jerk (pupil change acceleration), pupillary fluctuation trace, pupil area constriction latency, pupil area constriction velocity, pupil area dilation duration, spectral features, iris muscle features, iris muscle group identification, iris muscle fiber contractions, iris sphincter identification, iris dilator identification, iris sphincter symmetry, pupil and iris centration vectors, blink rate, blink duration, blink latency, blink velocity, partial blink rate, partial blink duration, blink entropy (deviation from periodicity), sclera segmentation, iris segmentation, pupil segmentation, stroma change detection, percent eyes closed, eyeball area (squinting), iridea changes;

wherein the hardware system comprises a processor configured to run a machine learning classification model and a computer vision model;

processing, by the computer vision model, image frames of the video to extract a first set of ocular signals elicited by the first stimuli and a second set of ocular signals elicited by the second stimuli, wherein the first set of ocular signals is processed separately from the second set of ocular signals as stimulus-specific ocular signal sets;

determining, by the processor, a differential ocular response by comparing the first set of ocular signals relative to the second set of ocular signals;

estimating, by an algorithm run by the machine learning classification model, a probability of the mental health state based at least in part on the differential ocular response between the first and second stimuli; and displaying, after the processing, the mental health state estimated by the software of the patient to the patient, or, sending the mental health state to a mental health professional via an electronic communication.

2. The method of claim 1, wherein the mental health state comprises a mental health disorder.

3. The method of claim 1, wherein the mental health state comprises a substance abuse disorder.

4. The method of claim 1, wherein the mental health states comprises a post-traumatic stress disorder.

5. The method of claim 1, wherein the mental health states comprises an anxiety disorder.

6. The method of claim 1, wherein the mental health states comprises a depressive disorder.

7. The method of claim 1, wherein the mental health states comprises an acute stress disorder.

8. The method of claim 1, wherein the mental health states comprises an acute stress reaction.

9. The method of claim 1, wherein the at least one ocular signal comprises at least two ocular signals.

10. The method of claim 1, wherein the at least one ocular signal comprises at least three ocular signals.

11. The method of claim 1, wherein the method is repeated after an initial diagnosis to measure a severity of the mental health disorder over a period of time.

12. The method of claim 1, wherein the method is repeated after an initial diagnosis to measure a severity of the mental health disorder over a period of time while the patient is receiving treatment in order to measure a treatment efficacy.

13. The method of claim 1, including storing the mental health state of the patient in a retrievable data retention system.

14. The method of claim 1, wherein the video camera, the electronic display screen, the hardware system and the software are configured to run on the hardware system which are all part of an electronic mobile device, a tablet, a desktop computer or a laptop computer.

15. The method of claim 1, wherein the video camera and electronic display screen are remotely disposed in relation to the hardware system and software configured to run the hardware system.

16. The method of claim 15, wherein the hardware system and software comprises a cloud-based system.

17. The method of claim 1, wherein the video camera is a webcam, a cell phone camera, or any other video camera with sufficient resolution and frame rate.

18. The method of claim 17, wherein the sufficient frame rate is 30 frames per second.

19. The method of claim 18, wherein the sufficient resolution is 100 pixels per inch.

20. The method of claim 1, including the step of measuring heart rate, wherein the estimating, by the algorithm run by the machine learning classification model, of the probability includes information from both the at least one ocular signal and the heart rate.

21. The method of claim 1, including the step of measuring respiration, wherein the estimating, by the algorithm run by the machine learning classification model, of the probability includes information from both the at least one ocular signal and the respiration.

22. The method of claim 1, including the step of measuring respiration and heart rate, wherein the estimating, by the algorithm run by the machine learning classification model, of the probability includes information from the at least one ocular signal, the heart rate and the respiration.

* * * * *